(12) United States Patent
Marecki et al.

(10) Patent No.: US 9,585,588 B2
(45) Date of Patent: Mar. 7, 2017

(54) ELECTRODE ASSEMBLY HAVING AN ATRAUMATIC DISTAL TIP

(71) Applicant: BOSTON SCIENTIFIC SCIMED, INC., Maple Grove, MN (US)

(72) Inventors: Andrew T. Marecki, Shrewsbury, MA (US); Michael C. Kozlowski, Wakefield, MA (US); Daniel J. Foster, Lino Lakes, MN (US); Mary M. Byron, Roseville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/718,909

(22) Filed: May 21, 2015

(65) Prior Publication Data

US 2015/0342491 A1 Dec. 3, 2015

Related U.S. Application Data

(60) Provisional application No. 62/007,320, filed on Jun. 3, 2014.

(51) Int. Cl.
| | |
|---|---|
| A61B 5/042 | (2006.01) |
| A61B 5/00 | (2006.01) |
| A61B 18/14 | (2006.01) |
| A61B 18/00 | (2006.01) |

(52) U.S. Cl.
CPC .......... *A61B 5/0422* (2013.01); *A61B 5/6858* (2013.01); *A61B 18/1492* (2013.01); *A61B 2018/0016* (2013.01); *A61B 2018/00267* (2013.01); *A61B 2018/00357* (2013.01); *A61B 2018/00577* (2013.01); *A61B 2018/00839* (2013.01); *A61B 2018/1467* (2013.01); *A61B 2562/12* (2013.01); *Y10T 29/49004* (2015.01)

(58) Field of Classification Search
CPC ................ A61B 5/0422; A61B 5/6958; A61B 2018/00267

See application file for complete search history.

(56) References Cited

U.S. PATENT DOCUMENTS

| | | |
|---|---|---|
| 4,649,924 A | 3/1987 | Taccardi |
| 4,674,518 A | 6/1987 | Salo |
| 4,840,182 A | 6/1989 | Carlson |

(Continued)

FOREIGN PATENT DOCUMENTS

| | | |
|---|---|---|
| CA | 2719329 A1 | 10/2009 |
| CN | 203017083 U | 6/2013 |

(Continued)

OTHER PUBLICATIONS

International Search Report and Written Opinion issued in PCT/US2015/032753, mailed Mar. 9, 2016, 17 pages.

(Continued)

*Primary Examiner* — Lee S Cohen
(74) *Attorney, Agent, or Firm* — Faegre Baker Daniels LLP

(57) ABSTRACT

A catheter including expandable electrode assembly having a distal cap that mechanically engages a locking feature provided on the distal ends of each of two or more flexible splines forming a portion of the expandable electrode assembly is described. The distal cap defines an atraumatic distal tip of the catheter. The catheter may be used in a cardiac mapping and/or ablation procedure.

10 Claims, 14 Drawing Sheets

(56) References Cited

U.S. PATENT DOCUMENTS

| | | |
|---|---|---|
| 4,920,490 A | 4/1990 | Isaacson |
| 5,156,151 A | 10/1992 | Imran |
| 5,284,142 A | 2/1994 | Goble et al. |
| 5,297,549 A | 3/1994 | Beatty et al. |
| 5,300,068 A | 4/1994 | Rosar et al. |
| 5,309,910 A | 5/1994 | Edwards et al. |
| 5,341,807 A | 8/1994 | Nardella |
| 5,381,333 A | 1/1995 | Isaacson et al. |
| 5,469,858 A | 11/1995 | Osborne |
| 5,480,422 A | 1/1996 | Ben-Haim |
| 5,499,981 A | 3/1996 | Kordis |
| 5,500,011 A | 3/1996 | Desai |
| 5,553,611 A | 9/1996 | Budd et al. |
| 5,568,809 A | 10/1996 | Ben-Haim |
| 5,577,502 A | 11/1996 | Darrow et al. |
| 5,588,429 A | 12/1996 | Isaacson et al. |
| 5,634,469 A | 6/1997 | Bruder et al. |
| 5,662,108 A | 9/1997 | Budd et al. |
| 5,687,737 A | 11/1997 | Branham et al. |
| 5,697,377 A | 12/1997 | Wittkampf |
| 5,704,365 A | 1/1998 | Albrecht et al. |
| 5,722,402 A | 3/1998 | Swanson et al. |
| 5,782,239 A * | 7/1998 | Webster, Jr. ......... A61B 5/0422 600/374 |
| 5,840,025 A | 11/1998 | Ben-Haim |
| 5,840,031 A | 11/1998 | Crowley |
| 5,846,198 A | 12/1998 | Killmann |
| 5,848,972 A | 12/1998 | Triedman et al. |
| 5,871,443 A * | 2/1999 | Edwards ............... A61B 5/0422 600/374 |
| 5,893,847 A | 4/1999 | Kordis |
| 5,896,847 A | 4/1999 | Usuki |
| 5,921,982 A | 7/1999 | Lesh et al. |
| 5,928,228 A * | 7/1999 | Kordis ................. A61B 5/0422 600/374 |
| 5,954,665 A | 9/1999 | Ben-Haim |
| 5,971,933 A | 10/1999 | Gopakumaran et al. |
| 5,983,126 A | 11/1999 | Wittkampf |
| 5,986,126 A | 11/1999 | Bunel et al. |
| 6,014,581 A | 1/2000 | Whayne et al. |
| 6,050,267 A | 4/2000 | Nardella et al. |
| 6,095,150 A | 8/2000 | Panescu et al. |
| 6,163,716 A | 12/2000 | Edwards et al. |
| 6,167,296 A | 12/2000 | Shahidi |
| 6,226,542 B1 | 5/2001 | Reisfeld |
| 6,236,886 B1 | 5/2001 | Cherepenin et al. |
| 6,240,307 B1 | 5/2001 | Beatty et al. |
| 6,246,898 B1 | 6/2001 | Vesely et al. |
| 6,254,536 B1 | 7/2001 | DeVito |
| 6,278,894 B1 | 8/2001 | Salo et al. |
| 6,298,257 B1 | 10/2001 | Hall et al. |
| 6,308,093 B1 | 10/2001 | Armoundas et al. |
| 6,314,310 B1 | 11/2001 | Ben-Haim et al. |
| 6,317,619 B1 | 11/2001 | Boernert et al. |
| 6,318,375 B1 | 11/2001 | Plicchi et al. |
| 6,360,123 B1 | 3/2002 | Kimchi et al. |
| 6,368,285 B1 | 4/2002 | Osadchy et al. |
| 6,400,981 B1 | 6/2002 | Govari |
| 6,516,807 B1 | 2/2003 | Panescu et al. |
| 6,547,082 B1 | 4/2003 | Babini |
| 6,556,695 B1 | 4/2003 | Packer et al. |
| 6,574,492 B1 | 6/2003 | Ben-Haim et al. |
| 6,574,498 B1 | 6/2003 | Gilboa |
| 6,593,884 B1 | 7/2003 | Gilboa et al. |
| 6,600,948 B2 | 7/2003 | Ben-Haim et al. |
| 6,603,996 B1 | 8/2003 | Beatty et al. |
| 6,631,290 B1 | 10/2003 | Guck et al. |
| 6,640,119 B1 | 10/2003 | Budd et al. |
| 6,650,927 B1 | 11/2003 | Keidar |
| 6,690,963 B2 | 2/2004 | Ben-Haim et al. |
| 6,701,176 B1 | 3/2004 | Halperin et al. |
| 6,728,562 B1 | 4/2004 | Budd et al. |
| 6,773,402 B2 | 8/2004 | Govari et al. |
| 6,807,439 B2 | 10/2004 | Edwards et al. |
| 6,839,588 B1 | 1/2005 | Rudy |
| 6,847,839 B2 | 1/2005 | Ciaccio et al. |
| 6,872,428 B2 | 3/2005 | Yang et al. |
| 6,892,090 B2 | 5/2005 | Verard et al. |
| 6,892,091 B1 | 5/2005 | Ben-Haim et al. |
| 6,893,588 B2 | 5/2005 | Lawson et al. |
| 6,939,309 B1 | 9/2005 | Beatty et al. |
| 6,957,101 B2 | 10/2005 | Porath et al. |
| 6,978,168 B2 | 12/2005 | Beatty et al. |
| 6,990,370 B1 | 1/2006 | Beatty et al. |
| 7,016,719 B2 | 3/2006 | Rudy et al. |
| 7,043,292 B2 | 5/2006 | Tarjan et al. |
| 7,198,635 B2 | 4/2007 | Danek et al. |
| 7,263,397 B2 | 8/2007 | Hauck et al. |
| 7,505,810 B2 | 3/2009 | Harlev et al. |
| 7,515,954 B2 | 4/2009 | Harlev et al. |
| 7,729,752 B2 | 6/2010 | Harlev et al. |
| 8,103,327 B2 | 1/2012 | Harlev et al. |
| 8,137,343 B2 | 3/2012 | Harlev et al. |
| 8,364,235 B2 | 1/2013 | Kordis et al. |
| 8,463,368 B2 | 6/2013 | Harlev et al. |
| 8,538,509 B2 | 9/2013 | Harlev et al. |
| 8,725,240 B2 | 5/2014 | Harlev et al. |
| 8,728,075 B2 | 5/2014 | Wu et al. |
| 8,825,130 B2 * | 9/2014 | Just ................. A61B 18/1492 600/374 |
| 9,014,793 B2 | 4/2015 | Harlev et al. |
| 2002/0151807 A1 | 10/2002 | Goldin |
| 2002/0177766 A1 | 11/2002 | Mogul |
| 2003/0018251 A1 | 1/2003 | Solomon |
| 2003/0065271 A1 | 4/2003 | Khoury |
| 2003/0076277 A1 | 4/2003 | Muramatsu et al. |
| 2003/0078509 A1 | 4/2003 | Panescu |
| 2003/0216630 A1 | 11/2003 | Jersey-Willuhn et al. |
| 2004/0077942 A1 | 4/2004 | Hall et al. |
| 2004/0097806 A1 | 5/2004 | Hunter et al. |
| 2004/0243015 A1 | 12/2004 | Smith et al. |
| 2004/0254437 A1 | 12/2004 | Hauck et al. |
| 2005/0033136 A1 | 2/2005 | Govari et al. |
| 2005/0038337 A1 | 2/2005 | Edwards |
| 2005/0054918 A1 | 3/2005 | Sra |
| 2005/0107834 A1 | 5/2005 | Freeman et al. |
| 2005/0154282 A1 | 7/2005 | Li et al. |
| 2005/0288599 A1 | 12/2005 | MacAdam et al. |
| 2006/0085049 A1 | 4/2006 | Cory et al. |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0083194 A1 | 4/2007 | Kunis et al. |
| 2007/0197929 A1 | 8/2007 | Porath et al. |
| 2007/0265539 A1 | 11/2007 | Hastings et al. |
| 2007/0270703 A1 | 11/2007 | He et al. |
| 2007/0287902 A1 | 12/2007 | Fuimaono et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0190438 A1 | 8/2008 | Harlev et al. |
| 2008/0221566 A1 | 9/2008 | Krishnan |
| 2008/0234588 A1 | 9/2008 | Feldman et al. |
| 2008/0249424 A1 | 10/2008 | Harlev et al. |
| 2009/0171274 A1 | 7/2009 | Harlev et al. |
| 2009/0177072 A1 | 7/2009 | Harlev et al. |
| 2009/0253976 A1 | 10/2009 | Harlev et al. |
| 2009/0299355 A1 | 12/2009 | Bencini et al. |
| 2010/0286551 A1 | 11/2010 | Harlev et al. |
| 2012/0277567 A1 | 11/2012 | Harlev et al. |
| 2013/0172715 A1 | 7/2013 | Just et al. |
| 2013/0274582 A1 | 10/2013 | Afonso et al. |
| 2013/0345538 A1 | 12/2013 | Harlev et al. |
| 2014/0018880 A1 | 1/2014 | Zarins et al. |
| 2014/0200442 A1 | 7/2014 | Harlev et al. |
| 2014/0238175 A1 | 8/2014 | Huszar et al. |
| 2014/0275921 A1 | 9/2014 | Harlev et al. |

(56) References Cited

U.S. PATENT DOCUMENTS

| | | | |
|---|---|---|---|
| 2015/0223726 | A1 | 8/2015 | Harlev |
| 2015/0351652 | A1 | 12/2015 | Marecki et al. |
| 2015/0374252 | A1 | 12/2015 | de la Rama et al. |

FOREIGN PATENT DOCUMENTS

| | | | |
|---|---|---|---|
| EP | 0779059 | B1 | 6/1997 |
| EP | 1484026 | A1 | 12/2004 |
| EP | 2265172 | A2 | 12/2010 |
| EP | 2269505 | B1 | 5/2012 |
| WO | WO9725917 | A1 | 7/1997 |
| WO | 2008097767 | A2 | 8/2008 |
| WO | 2009085108 | A1 | 7/2009 |
| WO | 2009123819 | A2 | 10/2009 |
| WO | 2013028998 | A2 | 2/2013 |
| WO | 2014110579 | A1 | 7/2014 |
| WO | 2015187386 | A1 | 12/2015 |
| WO | 2015187430 | A2 | 12/2015 |

OTHER PUBLICATIONS

Makela et al., "Revew of Cardiac Image Registration Methods", IEEE Transaction on Medical Imaging, 21(9):1011-1021, 2002.

Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252.

Mangan, Alan et al., "Partitioning 3D Surface Meshes Using Watershed Segmentation", IEEE Transactions on Visualization and Computer Graphics, 5(4):308-321, 1999.

Meininger et al. "Initial Experience with a Novel Focused Ultrasound Ablation System for Ring Ablation Outside the Vein", Journal of Interventional Cardiac Electrophysiology, 8:141-148, 2003.

Merrill, Daniel R. et al., "Electrical stimulation of excitable tissue: design of efficacious and safe protocols", Journal of Neuroscience Methods, 141:171-198, 2005.

Miller, "Editor's Forum—Application of Registration for Ablation: A Marriage of Technologies", Journal of Interventional Cardiac Electrophysiology, 11:87-89, 2004.

Nademanee et al., "A New Approach for Catheter Ablation of Atrial Fibrillation: Mapping of the Electrophysiologic Substrate", Journal of the American College of Cardiology, 43(11):2044-2053, 2004.

Non-Final Office Action in U.S. Appl. No. 11/451,908. dated Sep. 4, 2008, 12 pages.

Non-Final Office Action issued in U.S. Appl. No. 11/451,898 dated Sep. 25, 2008, 13 pages.

Noseworthy et al., "The Impact of Respiration on Left Atrial and Pulmonary Venous Anatomy: Implications for Image-Guided Intervention", Heart Rhythm, 2:1173-1178, 2005.

Pappone et al., "Robotic Magnetic Navigation for Atrial Fibrillation Ablation", Journal of the American College of Cardiology, 47(7): 1390-1400, 2006.

Paragios, "A Level Set Approach for Shape-Driven Segmentation and Tracking of the Left Ventricle", IEEE Transactions on Medical Imaging, 22(6):773-776, 2003.

Persson, "A Simple Mesh Generator in MATLAB", SIAM Review, 46(2):329-345, 2004.

Persson, "Mesh Generation for Implicit Geometrics", Massachusetts Institute of Technology—Thesis, Feb. 5, 2006.

Pham, Dzung, et al., "Current Methods in Medical Image Segmentation", Annu. Rev. Biomed. Eng., 02:315-337, 2000.

Rao et al., "Novel Noncontact Catheter System for Endocardial Electrical and Anatomical Imaging", Annals of Biomedical Engineering, 32(4):573-584, 2004.

Reddy et al., "Use of a Diode Laser Balloon Ablation Catheter to Generate Circumferential Pulmonary Venous Lesions in an Open-Thoracotomy Caprine Model", PACE, 27:52-57, 2004.

Reddy et al., "Integration of Cardiac Meagnetic Resonance Imaging with Three-Dimentional Electroanatomic Mapping to Guide Left Ventricular Catheter Manipulation—Feasibility is a Porcine Modelof Healed Myocardial Infarction", Journal of the American College of Cardiology, 44(11):2202-2213, 2004.

Sanders et al., "Spectral Analysis Identifies Sites of High-Frequency Activity Maintaining Atrial Fibrillation in Humans", Circulation, 112:789-797, 2005.

Sethian, "Level Set Methods and Fast Marching Methods: Evolving Interlaces in Computational Geometry, Fluid Mechanics, Computer Vision, and Materials Science", Department of Mathematics—University of California, Berkeley, Cambridge University Press, 1999.

Simon et al. "Electroanatomic Mapping of the Right Arm With a Right Atrial Basket Catheter and Three-Dimensional Intracardiac Echocardiography", PACE, 27: 318-326, 2004.

Smits et al., "Catheter-Based Intamyocarial Injection of Autologous Skeletal Myoblasts as a Primary Treatment of Ischemic Heart Failure", Journal of the American College of Cardiology, 42(12):2063-2069, 2003.

Solomon et al., "Real-Time Cardiac Catheter Navigation on Three-Dimensional CT Images", Journal of Interventional Cardiac Electrophysiology, 8:27-36, 2003.

Sra et al., "Registration of Three-Dimensional Left Atrial Computed Tomographic Images with Projection Images Obtained Using Fluoroscopy", Circulation, 112:3763-3768, 2005.

Sra, Jasbir et al, "Registration of 3D Computed Tomographic Images With Interventional Systems: Implications for Catheter Ablation of Atrial Fibrillation", J Intery Card Electrophysiol, 16:141-148, 2006.

Stevenson, "Radiofrequency Catheter Ablation of Ventricular Tachycardia After Myocardial Infarction", Circulation, 98:308-314, 1998.

Taccardi et al., "A New Intracavitary Probe for Detecting the Site of the Origin of Ectopic Ventricular Beats During One Cardiac Cycle", Circulation, 75(1):272-281, 1987.

Thal et al., "Novel Applications in Catheter Ablation", Journal of Inverventional Cardiac Electrophysiology, 13:17-21, 2005.

Thiagalingam et al., "Noncontact Mapping of the Left Ventricle: Insights from Validation With Transmural Contact Mapping", PACE, 27:570-578, 2004.

Voth, "The Inverse Problem of Electrocardiography: Industrial Solutions and Simulations", BEM and NFSI Conferernce Proceedings, Minneapolis, MN, May 12-15, 2005, pp. 191-194.

Wittkampf et al., "LocaLisa: New Technique for Real-Time 3-Dimensional Localization of Regular Intracardiac Electrodes", Circulation, 99:1312-1317, 1999.

Written Opinion of the International Searching Authority issued in PCT/US208/13553, mailed Feb. 5, 2009, 6 pages.

Yezzi, Anthony et al., "A Geometric Snake Model for Segmentation", IEEE Transactions on Medical Imaging, 16(2) Apr. 1997.

Written Opinion of International Searching Authority issued in PCT/US2009/061277, mailed Apr. 3, 2010, 10 pages.

Adams et al., "Seeded Region Growing", IEEE Transactions on Pattern Analysis and Machine Intelligence, 16(6):641-647, 1994.

Arthur, "Clinical Use of Intracardiac Impedance: Current Applications and Future Perspectives", PACE, vol. 24:500-506, Apr. 2001.

Authorized officer Carl H. Layno, International Search Report and the Written Opinion in PCT/US07/70854 mailed Sep. 12, 2008, 15 pages.

Authorized officer Lee W. Young, International Search Report and the Written Opinion in PCT/US08/52385 mailed Aug. 8, 2008, 11 pages.

Authorized officer, Blaine R. Copenheaver, International Search Report and the Written Opinion in PCT/US2009/061277 mailed Apr. 8, 2010, 13 pages.

Baan, Jan et al., "Continuous Measurement of Left Ventricular Volume in Animals and Humans by Conductance Catheter", Circulation, 07(5):812-823, 1984.

Badics, "Real-Time Reconstruction of Endocardial Potential Maps in Non-Contact Cardiace Mapping", International Journal for computation and Mathematics in Electrical Engineering (COMPEL), vol. 28, No. 4, 2009.

Ben-Haim et al., "Nonfluoroscopic, in Vivo Navigation arid Mapping Technoiogy", Nature Medicine, 2(12):1393-1395, 1996.

(56) References Cited

OTHER PUBLICATIONS

Besl et al., "A Method for Registration of 3-D Shapes", IEEE Transaction on Pattern Analysis and Machine Intelligence 14(2):239-256, 1992.
Blomstrorn-Lundqvist et al., "ACC/AHA/ESC Guidelines for the Management of Patients with Supraventricular Arrhythmias-Executive Summary", Journal of the American College of Cardiology, 42(8)1493-1531, 2003.
Breithardt et al., "AHA Medical/Scientific Statement—Special Report: Standards for Analysis of Ventricular Late Potentials Using High-Resolution or Signal/Averaged Electrocardiography", Circulation, 83(4):1481-1488, 1991.
Brooks et al., "Electrical Imaging of the Heart", IEEE Signal Processing Magazine, pp. 24-42, 1997.
Caspi et al., "Stem Cell Research: Regenerating the Heart Using Human Embryonic Stem Cells—from Cell to Bedside", IMAJ 8:208-214, 2006.
Cheney et al, "Electrical Imedance Tomography," SIAM Review 41, pp, 85-101, 1999.
Communication pursuant to Article 94(3) EPC in European Application No. 07798369, mailed Nov. 17, 2011, 5 pages (0002EP1).
De Groot et al., "Three-Dimensional Catheter Positioning During Radiofrequency Ablation in Patients: First Application of a Real-Time Position Management System", Journal of Cardiovascular Electrophysiology, 11:1183-1192, 2000.
Donahue et al., "Focal Modification of Electrical Conduction in the Heart by Viral Gene Transfer", Nature Medicine, 6 (12):1395-1398, 2000.
Dong et al., "Integrated Electroanatornic Mapping With Three-Dimensional Computed Tomographic Images for Real-Time Guided Ablations", Circulation 113:186-194, 2006.
Durrer et al., "Total Excitation of the Isolated Human Heart", Circulation, XL1:899-912, 1970.
Ector, Joris et al., "Cardiac Three-Dimensional Magnetic Resonance Imaging and Fluoroscopy Merging", Circulation, 112:3769-3776, 2005.
European Search Report issued in EP Application No. 12815179.2, mailed Apr. 28, 2015, 6 pages.
Extended European Search Report issued in EP Application No. 09727423.7, mailed May 15, 2012, 5 pages.
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart, 87:575-582, 2002.
Geddes et al., "Criteria for the Selection of Materials for Implanted Electrodes," Annals of Biomedical Engineering 31:879-890, 2003.
Gepstein et al., "A Novel Method for Nonfluoroscopic Catheter-Based Electroanatomical Mapping of the Heart", Circulation 95:1611-1622 1997.
Haug. E. J. et al.: Design Sensitivity Analysis of Structural Systems, Mathematics in Science and Engineering, vol. 177 (1986).
Huang, Yi-Chih et al., "Development of a Third Generation lntraventricular Impedance Imaging (Iii) System Evaluation of Hardware Design", Engineering in Medicine and Biology Society, Proceedings of the 19th Annual Internal Conference of the IEEE/EMBS, 6:2442-2444 Oct. 30-Nov. 2, 1997.
International Preliminary Report on Patentability issued in PCT/US2008/013553, mailed Feb. 5, 2009, 6 pages.
International Preliminary Report on Patentability issued in PCT/US2008/052385, mailed Aug. 8, 2008, 6 pages.
International Preliminary Report on Patentability issued in PCT/US2009/036099, mailed Oct. 14, 2010, 20 pages.
International Search Report and Written Opinion issued in PCT/US2009/036099, mailed Apr. 28, 2009, 21 pages.
International Search Report and Written Opinion issued in PCT/US2014/060137, mailed Dec. 10, 2014, 11 pages.
Jain et al., "Cell Therapy Attenuates Deleterious Ventricular Remodeling and Improves Cardiac Performance after Myocardial Infarction", Circulation, 103:1920-1927, 2001.
Jalife, "Rotors and Spiral Waves in Atrial Fibrillation", Journal of Cardiovascular Electrophysiology, 14:776-780, 2003.
Jane et al., Alignment Methods for Averaging of High-Resolution Cardiac Signals: A Comparative Study of Performance, IEEE Transaction on Biomedical Engineering, 38(6):571-579, 1991.
Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.
Kikuchi et al., "Targeted Modification of Atrial Electrophysiology by Homogeneous Transmural Artial Gene Transfer", Circulation, 111:264-270, 2005.
Kistler et al., "Validation of Three-Dimensional Cardiac Image Integration: Use of Integrated CT Image into Electroanatomic Mapping System to Performa Catheter Ablation of Atrial Fibrillation", Journal of Cardiovascular. Electrophysiology, 17:341-348, 2006.
Kuklik et al., The reconstruction, from a set of points, and analysis of the interior surface of the heart chamber, Physiological Measurement 25, pp. 617-627, 2004.
Kun Stevan et al., "Conductance Volumetric Model of an Eccentrically Positioned Catheter within a Three-Compartment Ellipsoidal Ventricle", U, IEEE Transactions on Jun. 1993, 40(6); 589-592.
L. Piegi, W. Tiller: The NURBS Book, 2nd Edition, Springer (1997).
Laciar et al., "Improved Alignment Method for Noisy High-Resolution ECG and Holter Records Using Multiscale Cross-Correlation", IEEE Transactions on Biomedical Engineering, 50(3):344-353, 2003.
Liu et al., "Endocardial Potential Mapping from a Noncontact Nonexpandable Catheter: A Feasibility Study", Annals of Biomedical Engineering, 26:994-1009, 1998.
Lorensen et al., "Marching Cubes: A High Resolution 3D Surface Construction Algorithm", Computer Graphics 21(4):163-169, Jul. 1987.
International Preliminary Report on Patentabiiity issued in PCT/US2014/060137, mailed Apr. 28, 2016, 9 pages.
International Search Report and Written Opinion issued in PCT/US2015/032004, mailed Sep. 4, 2015, 8 pages.
International Preliminary Report on Patentability issued in PCT/US2015/032004, issued on Dec. 6, 2016, 7 pages.
International Preliminary Report on Patentability issued in PCT/US2015/032753, issued on Dec. 6, 2016, 10 pages.

\* cited by examiner

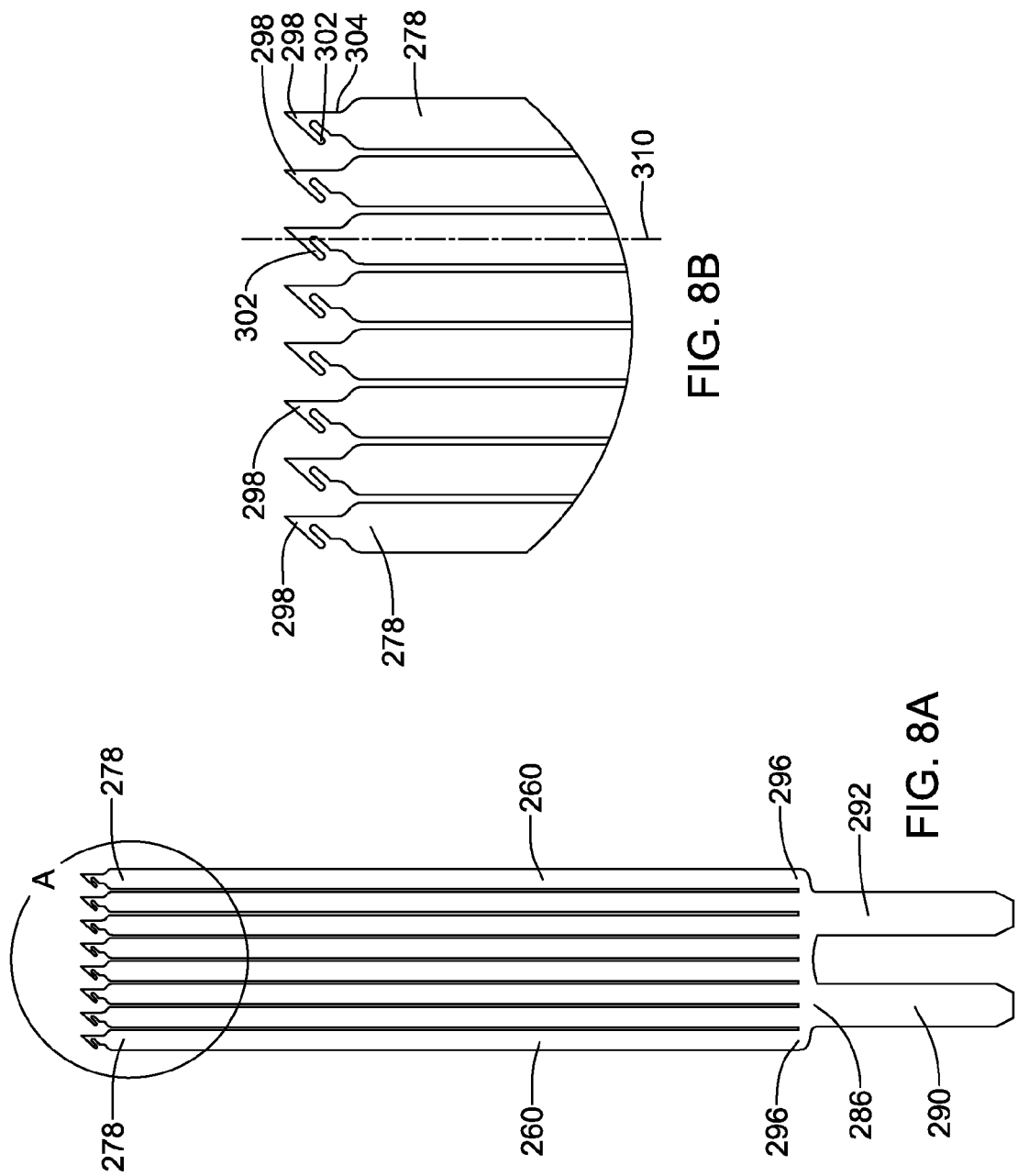

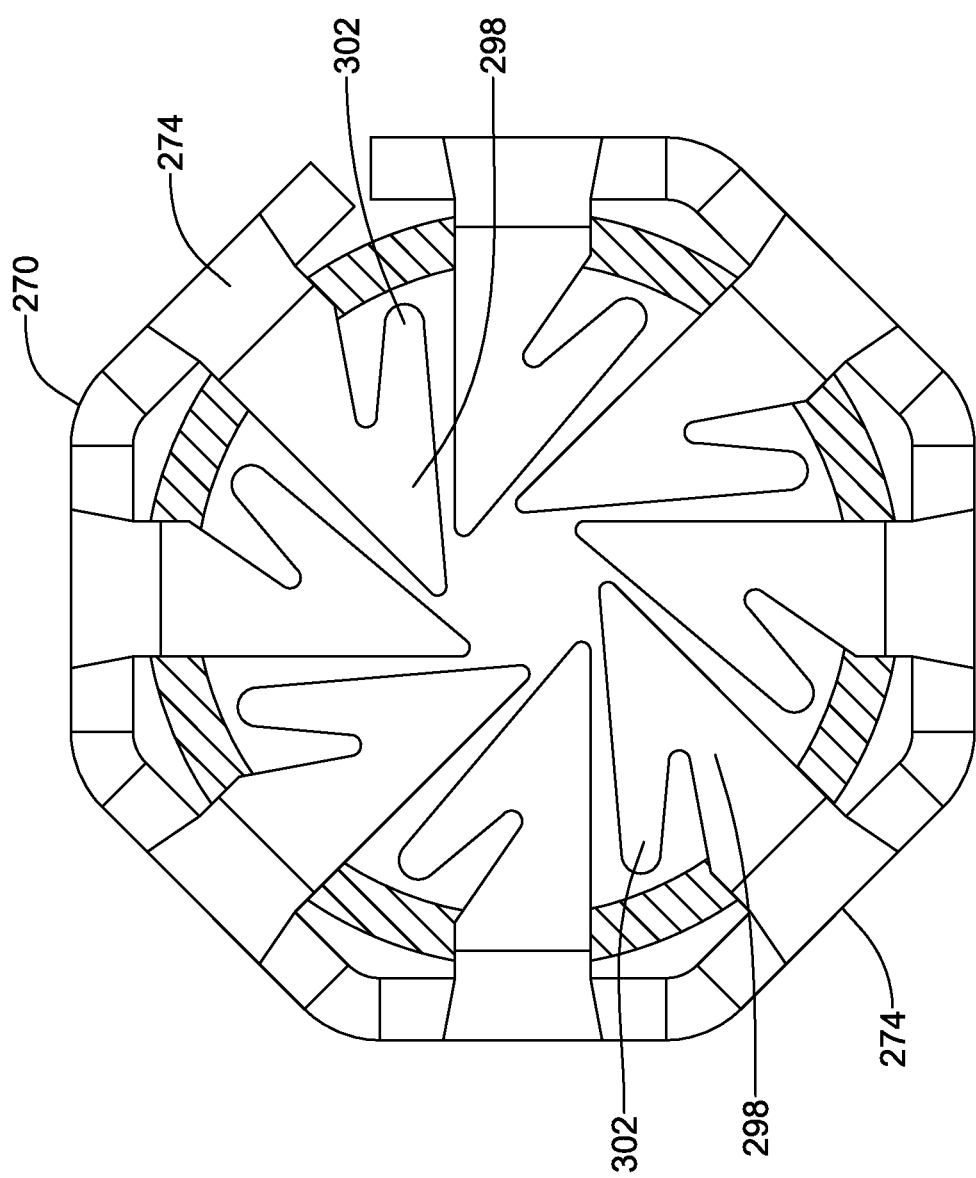

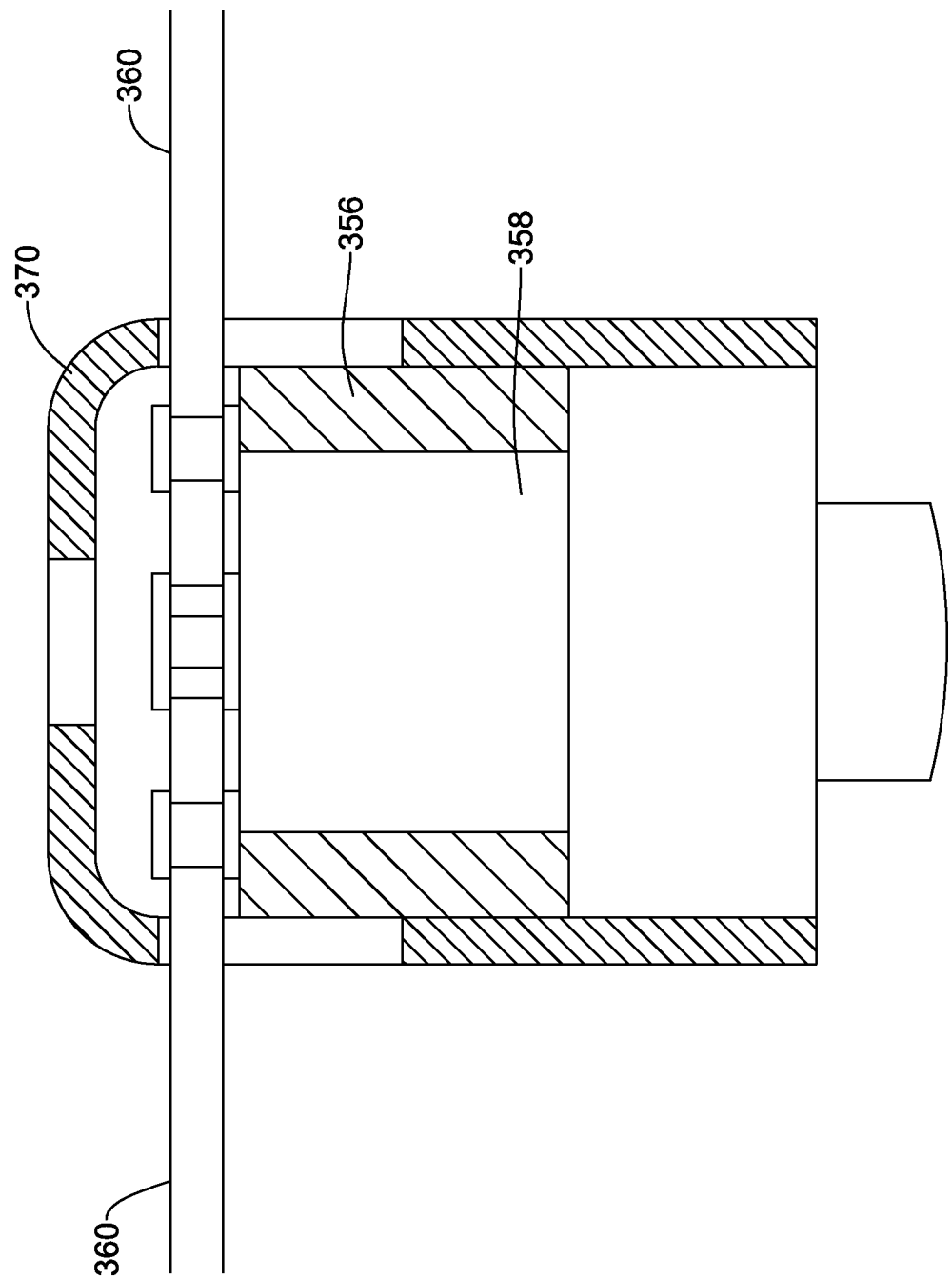

ELECTRODE ASSEMBLY HAVING AN ATRAUMATIC DISTAL TIP

CROSS-REFERENCE TO RELATED APPLICATIONS

This application claims priority under 35 U.S.C. §119 to U.S. Provisional Application Ser. No. 62/007,320, filed Jun. 3, 2014, the entirety of which is incorporated herein by reference.

TECHNICAL FIELD

The present disclosure generally relates to electrode assemblies for use in cardiac procedures and more particularly, to an electrode assembly that may be utilized in a cardiac mapping procedure.

BACKGROUND

Electrophysiology catheters are used in a variety of diagnostic and/or therapeutic medical procedures to diagnose and/or correct conditions such as cardiac arrhythmias, including for example, atrial tachycardia, ventricular tachycardia, atrial fibrillation, and atrial flutter. Cardiac arrhythmias are a leading cause of stroke, heart disease, and sudden death. The physiological mechanism of arrhythmia involves an abnormality in the electrical conduction of the heart. There are a number of treatment options for patients with arrhythmia that include medication, implantable devices, and catheter ablation of cardiac tissue.

SUMMARY

The present disclosure generally relates to electrode assemblies for use in cardiac procedures and more particularly, to an electrode assembly that may be utilized in a cardiac mapping procedure.

In a first example, a catheter is disclosed. The catheter includes an elongate catheter body extending from a proximal end to a distal end. An expandable electrode assembly is disposed at the distal end of the catheter body. The electrode assembly comprises a plurality of flexible splines extending from the distal end of the catheter body to a distal cap. The distal cap comprises a plurality of slots disposed about an outer circumference of the distal cap. The plurality of flexible splines includes at least a first spline comprising a distal end defining a locking feature secured within one of the plurality of slots provided in the distal cap. The expandable electrode assembly is configured to be transitioned between a collapsed configuration suitable for delivery and an expanded configuration. Two or more electrodes are located on the first spline.

In addition or alternatively, and in a second example, the distal cap comprises a cylindrical shape defining an interior cavity.

In addition or alternatively, and in a third example, the distal cap comprises a rounded tip having an aperture defined therein.

In addition or alternatively, and in a fourth example, a height is greater than a width for each of the slots.

In addition or alternatively, and in a fifth example, a width is greater than a height for each of the slots.

In addition or alternatively, and in a sixth example, the locking feature defined by the distal end of the first spline comprises a first portion having a first width and a second portion having a second width, the first width greater than the second width.

In addition or alternatively, and in a seventh example, the locking feature defined by the distal end of the first spline comprises an aperture formed therein.

In addition or alternatively, and in an eighth example, an adhesive is disposed within the distal cap.

In addition or alternatively, and in a ninth example, the distal cap comprises a rounded distal end and defines an atraumatic distal tip of the catheter.

In addition or alternatively, and in a tenth example, each of the slots are spaced an equal distance from one another about the outer circumference of the distal cap.

In addition or alternatively, and in an eleventh example, an actuation member is coupled to the expandable electrode assembly.

In addition or alternatively, and in a twelfth example, the locking feature defined by the distal end of the first spline comprises a hook shape.

In addition or alternatively, and in a thirteenth example, the locking feature defined by the distal end of the first spline comprises an arrowhead shape.

In addition or alternatively, and in a fourteenth example, the distal cap serves as a distal tip electrode.

In a fifteenth example, a catheter is disclosed. The catheter includes an elongate catheter body extending from a proximal end to a distal end. An expandable electrode assembly is disposed at the distal end of the catheter body. The electrode assembly comprises a plurality of flexible splines including a first spline extending from the distal end of the catheter body to a distal cap. The distal cap comprises a plurality of slots including a first slot disposed about an outer circumference of the distal cap. The first spline comprises a distal end defining a locking feature secured within the first slot. The expandable electrode assembly is configured to be transitioned between a collapsed configuration suitable for delivery and an expanded configuration. Two or more electrodes are located on the first spline. An actuation member is coupled to the expandable electrode assembly.

In a sixteenth example, a method of forming an expandable basket electrode assembly is disclosed. The method includes forming a flattened spline array comprising two or more flexible splines, a distal end of each spline defining a locking feature; forming a cylindrical spline array from the flattened spline array; positioning a distal cap comprising two or more slots disposed about an outer circumference adjacent a distal end of the cylindrical spline array; separating a first spline from the two or more flexible splines of the cylindrical spline array; rotating the first spline about its major axis from a first orientation to a second orientation; bending the first spline along its minor axis while it is in its second orientation and inserting the distal end into a first slot of the distal cap; and returning the first spline to its original first orientation.

In addition or alternatively, and in a seventeenth example, the first spline automatically returns from the second orientation to the first orientation.

In addition or alternatively, and in an eighteenth example, rotating the first spline about its major axis comprises rotating the first spline about 60 degrees to about 120 degrees about its major axis.

In addition or alternatively, and in a nineteenth example, the method further comprises separating a second spline from the two or more flexible splines of the cylindrical spline array; rotating the second spline about its major axis from the first orientation to the second orientation; inserting the distal end of the second spline while it is in the second orientation into a second slot; and returning the second spline from the second orientation to the first orientation.

In addition or alternatively, and in a twentieth example, the method further comprises delivering a potting material into the distal cap.

In addition or alternatively, and in a twenty-first example, the method further comprises inserting a cylindrical tube, plug, or gasket into the proximal end of the distal cap to occlude the gaps in the cap's slots, proximal to the distal ends of the splines.

In a twenty-second example, a method of forming a flexible electrode assembly is disclosed. The method includes: forming a first flexible printed circuit comprising one or more electrodes on an upper surface of a substrate and forming a second flexible printed circuit comprising one or more electrodes on a lower surface of the substrate to produce a flexible layered sheet; separating the flexible layered sheet into two or more splines extending longitudinally from a proximal end of the flexible layered sheet to a distal end of the flexible layered sheet, wherein the two or more splines are fully separated from one another such that they are not connected and at least one of the splines includes two or more electrodes; inserting a first end of a first spline of the two or more splines into a first slot provided in a distal cap; and inserting a first end of a second spline of the two or more splines into a second slot provided in the distal cap.

In addition or alternatively, and in a twenty-third example, the substrate comprises a shape memory material.

In addition or alternatively, and in a twenty-fourth example, the step of separating the flexible layered sheet into two or more splines comprises laser cutting the flexible layered sheet into two or more splines.

In addition or alternatively, and in a twenty-fifth example, the step of separating the flexible layered sheet into two or more splines comprises die cutting the flexible layered sheet into two or more splines.

In addition or alternatively, and in a twenty-sixth example, the method further includes securing a second end of the first spline and a second end of the second spline to a distal end of a catheter body to form an expandable electrode assembly, wherein the expandable electrode assembly is capable of transitioning from a collapsed configuration to an expanded configuration.

In addition or alternatively, and in a twenty-seventh example, the method further including at least partially rotating the first end of the first spline to facilitate insertion of the first end into the first slot provided in the distal cap and at least partially rotating the first end of the second spline to facilitate insertion of the first end of the second spline into the second slot provided in the distal cap.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 8A is a schematic view of another exemplary flattened array of multiple flexible splines;

FIG. 8B is a close-up, schematic view of the distal ends of each of the splines of the flattened array shown in FIG. 8A.

FIG. 9B is a cross-sectional view of the distal portion of the exemplary electrode assembly shown in FIG. 9A taken along lines A-A;

FIG. 10 is a cross-sectional view of the distal portion of another exemplary electrode assembly including a distal cap having a cylindrical plug inserted therein;

Figure 1:
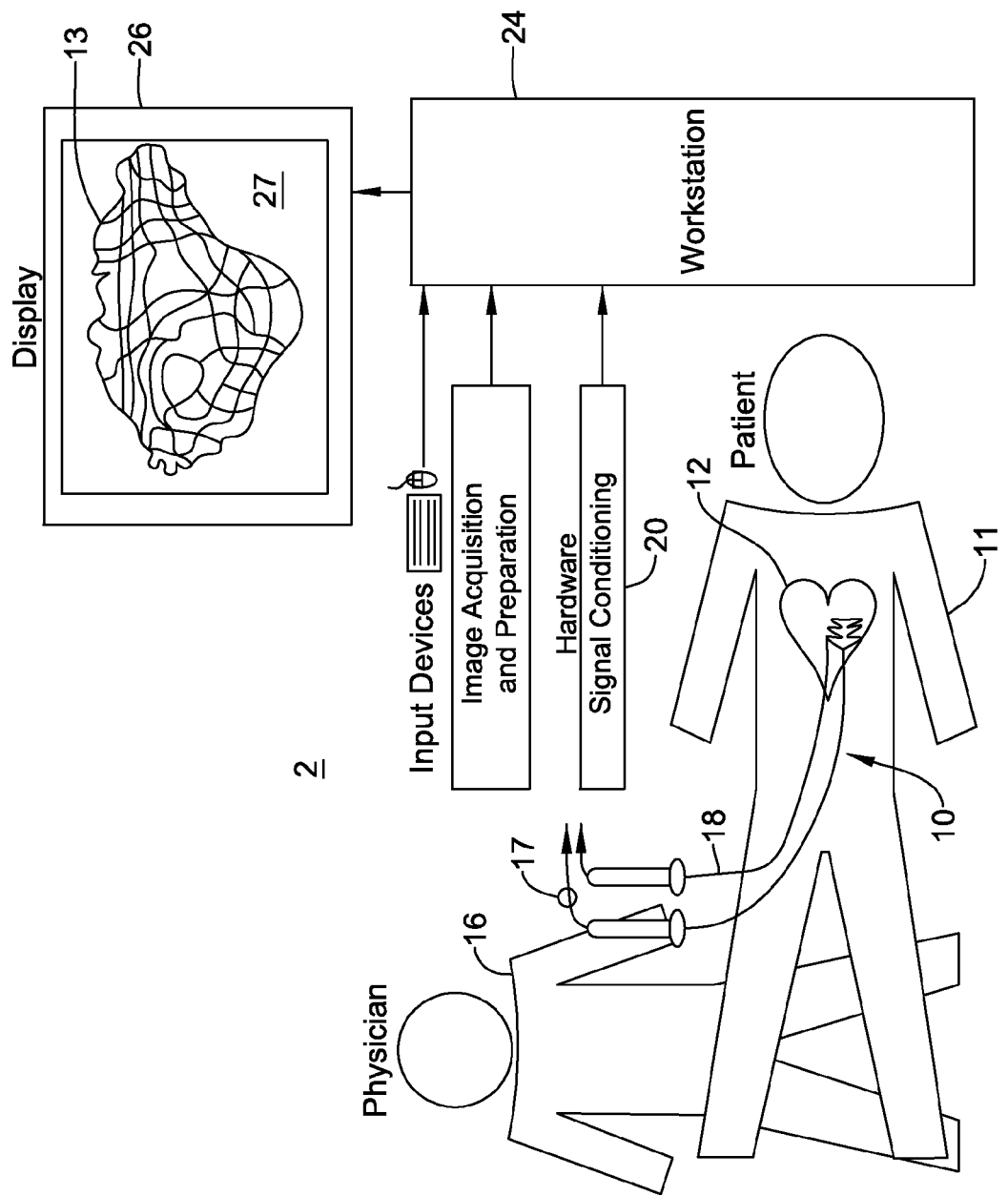
FIG. 1 is a schematic diagram showing a catheter in the context of a system.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

FIG. 1 is a high level, schematic view of an overall system 2 that includes a physician, a patient, catheters, including a mapping catheter 10, and related electrophysiology equipment located within an operating room. A physician 16 introduces the catheter 10 into the vasculature of the patient 11 at the patient's leg and advances it along a blood vessel ultimately, entering the patient's heart 12. Other catheters that may be used in the procedure are represented by companion catheter 18. Each catheter 10, 18 is coupled to signal conditioning hardware 20 with appropriate catheter cabling typified by catheter cable 17. The signal conditioning hardware 20 performs various interface functions applicable to the mapping, tracking, and registration procedures that are performed in conjunction with the workstation 24. If the companion catheter 18 is an ablation catheter, then conditioning hardware also forms an interface to an RF ablation unit (not illustrated).

In use, the physician looks at a computer display 26. Present on the display 26 is a substantial amount of information. A large window presents an image of the heart chamber 13 along with an image of the catheter 10. The physician will manipulate and control the catheter 10 based in part on the images and other data presented on the display 26. The image 27 seen in FIG. 1 is schematic and depicts the distal array of the deployed catheter 10 occupying a small portion of the heart chamber 13 volume. The representation of the heart chamber 13 may use color, wire frame, or other techniques to depict the structure of the heart chamber 13 and to simultaneously portray electrical activity of the patient's heart. In some cases, it may be useful to display chamber geometry, catheter location, and electrical activity in an integrated fashion on the display 26. In use, the physician will observe the display 26 and interact with the workstation processing unit 24 and the catheters 10 and 18, to direct a medical procedure such as, for example, a cardiac mapping procedure.

Figure 2A:
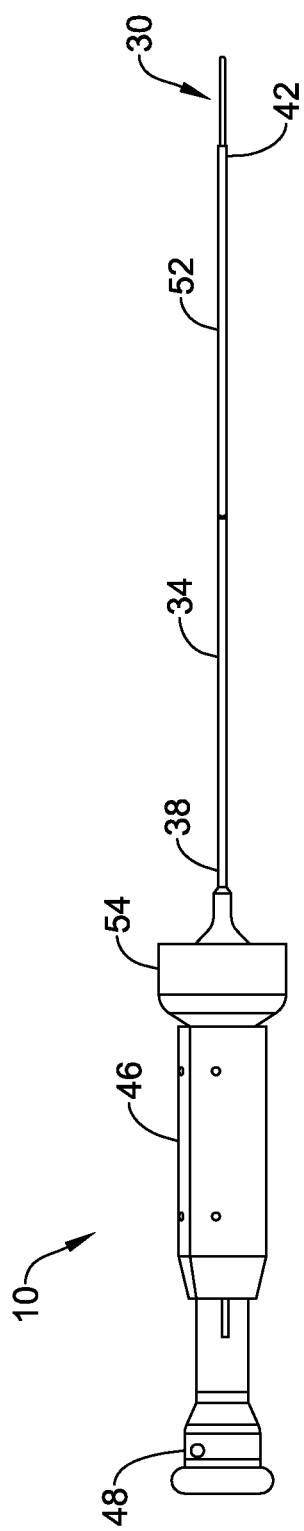
FIGS. 2A-2B are schematic views of an exemplary catheter.
Figure 2B:
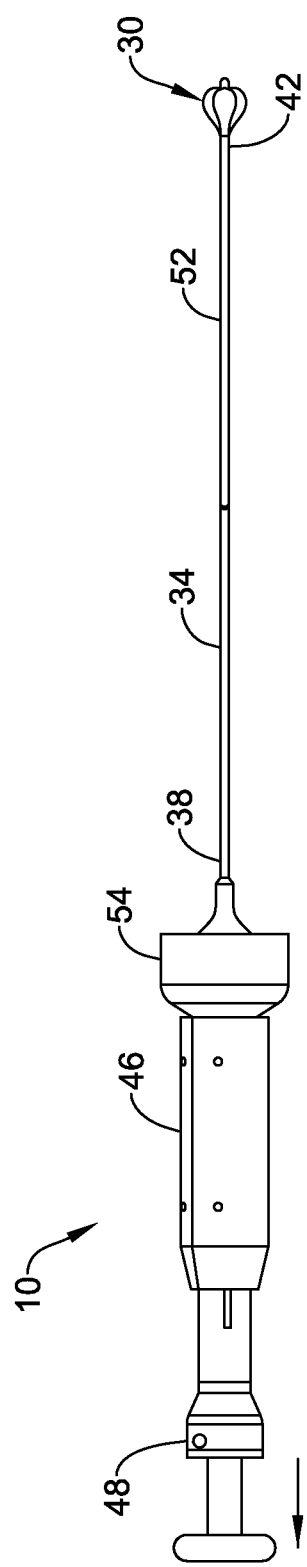

FIGS. 2A and 2B are schematic views of an exemplary intravascular catheter 10. In some cases, the catheter 10 may be used to map electro-anatomical characteristics of the heart in a cardiac mapping procedure. The mapping procedure may be an in-contact mapping or a non-contact mapping procedure. The catheter 10 may be deployed at a target location within a patient's heart, placing multiple electrodes in a known spatial configuration. Electrode stability and the known spatial geometry of the electrodes may improve the accuracy of the mapping device. Alternatively, the catheter 10 may be used in an ablation procedure. These are just some examples.

As shown in FIGS. 2A and 2B, the catheter 10 includes an elongate catheter body 34 extending from a proximal end 38 to a distal end 42. In addition, the catheter body 34 may include a lumen (not shown) extending there through, but this is not required in all embodiments. The catheter body 34 may have sufficient flexibility so as to navigate the tortuous pathways of a patient's vasculature system. The catheter 10 can include a handle assembly 46 coupled to the proximal end 38 of the catheter body 34. A physician may manipulate the handle assembly 46 to deliver, steer, rotate, deploy and/or deflect the catheter 10 when performing a medical procedure.

Additionally, as shown in FIGS. 2A and 2B, the catheter 10 may include an expandable electrode assembly 30 including one or more electrodes that may be used for cardiac mapping or diagnosis, ablation and/or other therapies involving the application of electrical energy to a patient's heart. In some cases, the handle assembly 46 may include a first actuation mechanism 48 that may be manipulated to transition the expandable electrode assembly 30 from a collapsed configuration (shown in FIG. 2A) suitable for delivery of the catheter 10 to a target location within a patient's body (e.g. the heart) and an expanded configuration (shown in FIG. 2B) suitable for use in a diagnostic procedure and/or delivery of a therapy. In some cases, the actuation mechanism 48 may include a pull wire that may be coupled to the expandable electrode assembly 30 that, when actuated in a proximal direction as indicated by the arrow shown in FIG. 2B, causes the expandable electrode assembly 30 to transition from the collapsed configuration to the expanded configuration. In other cases, the actuation mechanism 48 may include a retractable sheath that, when retracted in a proximal direction as indicated by the arrow shown in FIG. 2B, may permit the expandable electrode assembly 30 to self-expand from the collapsed configuration to the expanded configuration. These are just some examples of exemplary actuation mechanisms that may be utilized to facilitate expansion of the expandable electrode assembly 30 when the catheter 10 is in use. In some cases, the catheter body 34 may include a deflectable distal portion 52 that a physician may manipulate using a second actuation mechanism 54 provided in the handle assembly 46 to position the electrode assembly 30 nearer or adjacent to tissue of interest.

Figure 3A:
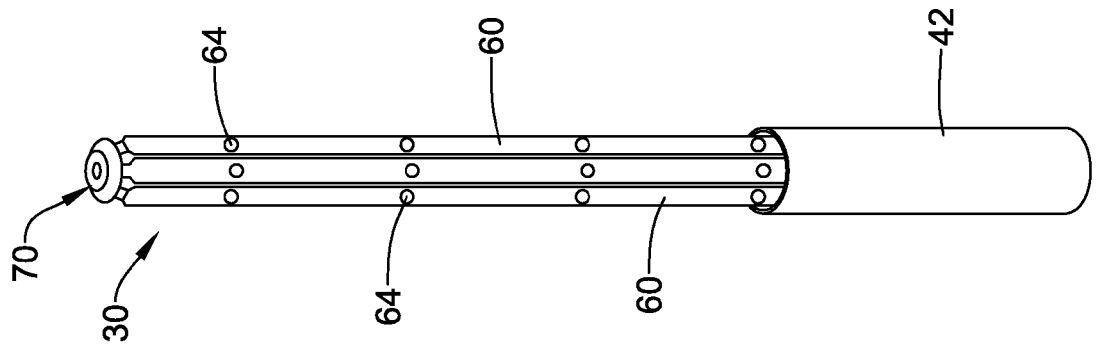
FIG. 3A is an isometric view of an expandable electrode assembly shown in a collapsed configuration.
Figure 3B:
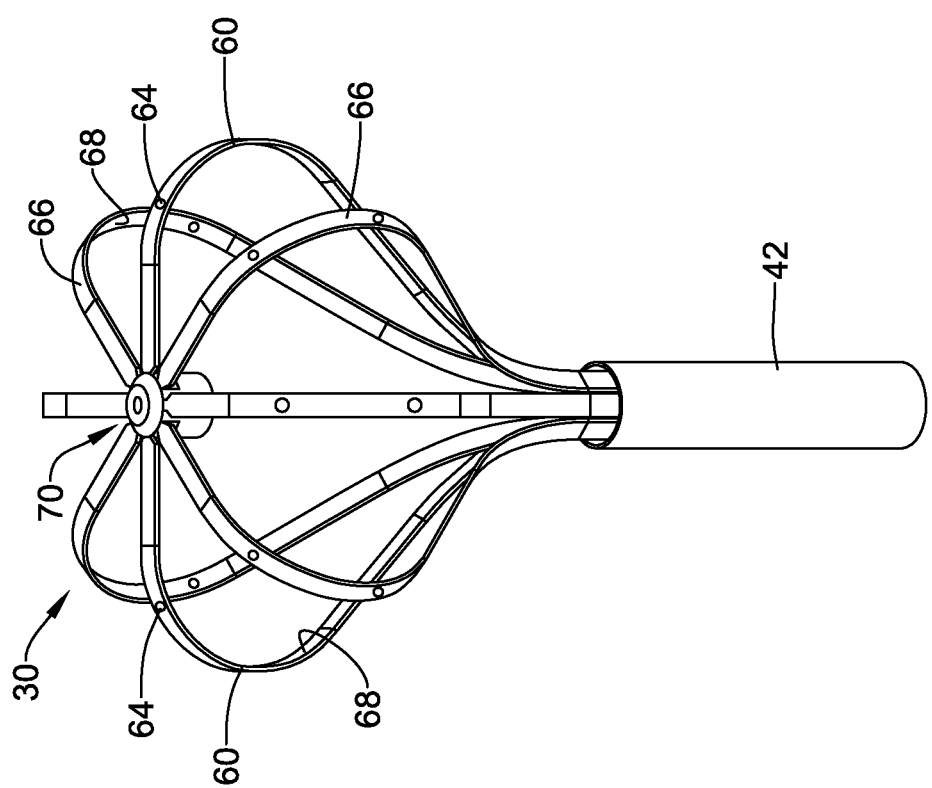
FIG. 3B is an isometric view of the expandable electrode assembly of FIG. 3A shown in an expanded configuration.

FIGS. 3A and 3B show different views of an exemplary expandable electrode assembly 30. As shown in FIGS. 3A and 3B, the expandable electrode assembly 30 is capable of being transitioned form a generally cylindrical, collapsed configuration suitable for delivery of the catheter 10 and the electrode assembly 30 to a target location within the patient's heart and an expanded configuration suitable for use in a desired cardiac procedure such as, for example, a mapping or ablation procedure.

As shown in FIGS. 3A and 3B, the expandable electrode assembly 30 may include two or more flexible splines 60 which may be capable of being flexed outwardly and away from a longitudinal axis of the electrode assembly 30. In some cases, as discussed herein, an actuation mechanism may be utilized to transition the electrode assembly 30 including the two or more flexible splines 60 from the collapsed configuration (FIG. 3A) to the expanded configuration (FIG. 3B). In other cases, the flexible splines 60 may be incorporate a shape memory material that may facilitate self-expansion of the flexible splines 60 and consequently, the electrode assembly 30, from the collapsed configuration to the expanded configuration. The flexible splines 60 may be relatively stiff such that the electrode assembly 30 may be expanded into a known, reproducible shape capable of retaining a known spatial geometry when in use which, in some cases, may be aided by the incorporation of a shape-memory material or other stiff polymeric material such as, for example, a nickel-titanium alloy, or a polyimide or PEEK into the flexible splines 60. Alternatively, depending upon the desired application, the flexible splines 60 may be fabricated such that they are somewhat compliant so as to conform to a surface of a patient's heart when placed into intimate contact with the surface of the patient's heart.

The expandable electrode assembly 30 may include a number of electrodes 64 located on each of the flexible splines 60 forming an electrode array. In many cases, the electrodes 64 may be sensing electrodes. In addition, the electrode assembly 30 may include at least some current injecting locator electrodes. The locator electrodes may be positioned diametrically opposed to each other on the meridian of the expanded electrode assembly 30. The electrode assembly 30 may also include a tip electrode which may be used for cardiac stimulation, ablation or as a locator electrode.

Each electrode 64 may be electrically connected to the cabling in the handle assembly 46. In some cases, the signal from each individual electrode may be independently available at the hardware interface 20. This may be achieved by passing a conductor for each electrode through a connection cable extending within the catheter body. As an alternative, the signals may be multiplexed to minimize the number of conductors.

The electrodes 64 may have a uniform and symmetrical distribution throughout the expandable electrode assembly 30. In other cases, the electrodes 64 may have an asymmetrical distribution throughout the expandable electrode assembly 30. Certain electrode distributions may be advantageous for non-contact cardiac mapping, while others may be more suited for contact mapping. The number of electrodes 64 distributed throughout the electrode assembly 30 and the stability of the shape of electrode assembly 30, when expanded, may affect the overall performance of the mapping system.

The electrodes 64 may be located on the outer surfaces 66 of each or the splines 60, the inner surfaces 68 of each of the splines 60, or both the outer and inner surfaces 66, 68 of each of the flexible splines 60. In some cases, up to sixty-four sensing electrodes 64 may be distributed over and along the various splines 60. Depending upon the application, the electrode assembly 30 may include fewer or greater than sixty-four electrodes. In some cases, the electrodes 64 may form a number of bipolar electrode pairs. The bipolar electrode pairs may be formed between two adjacent electrodes located on the same surface (inner or outer surface) of a spline, between two electrodes located on adjacent splines, or between a first electrode located on an outer surface opposite a second electrode located on an inner surface of a spline. In some cases, all of the electrodes 64 located on the flexible splines 60 may be paired together to form a plurality of electrode pairs distributed along the length of the individual flexible splines 60. Up to thirty-two bipolar electrode pairs may be distributed throughout the electrode assembly 30 for a total of up to sixty-four electrodes 64 depending upon the overall size and geometry of the electrode assembly 30. However, it is contemplated that the electrode assembly 30 may be configured such that it is capable of carrying fewer or greater than thirty-two bipolar electrode pairs, depending upon the overall size and geometry of the electrode assembly 30 and the desired application.

Referring now back to FIGS. 3A and 3B, each of the flexible splines 60 may extend from a distal end 42 of the catheter body 34 to a distal cap 70. The distal cap 70 may have a rounded distal end, and may define an atraumatic distal tip of the catheter 10. As will be described in greater detail herein, at least one of the flexible splines 60 may be mechanically interlocked with a corresponding slot provided in the distal cap 70 such that there is a one to one mechanical engagement between the flexible spline 60 and a corresponding slot provided in the cap 70. In some cases, each of the flexible splines 60 may be mechanically interlocked with a corresponding slot provided in the distal cap 70 such that there is a one to one mechanical engagement between each flexible spline 60 and each slot provided in the cap 70. An adhesive may be utilized to provide a secondary means of securing the each of the flexible splines within each of their respective slots. In some cases, the distal cap 70 may serve as a tip electrode, but this is not required in all embodiments.

Figure 4:
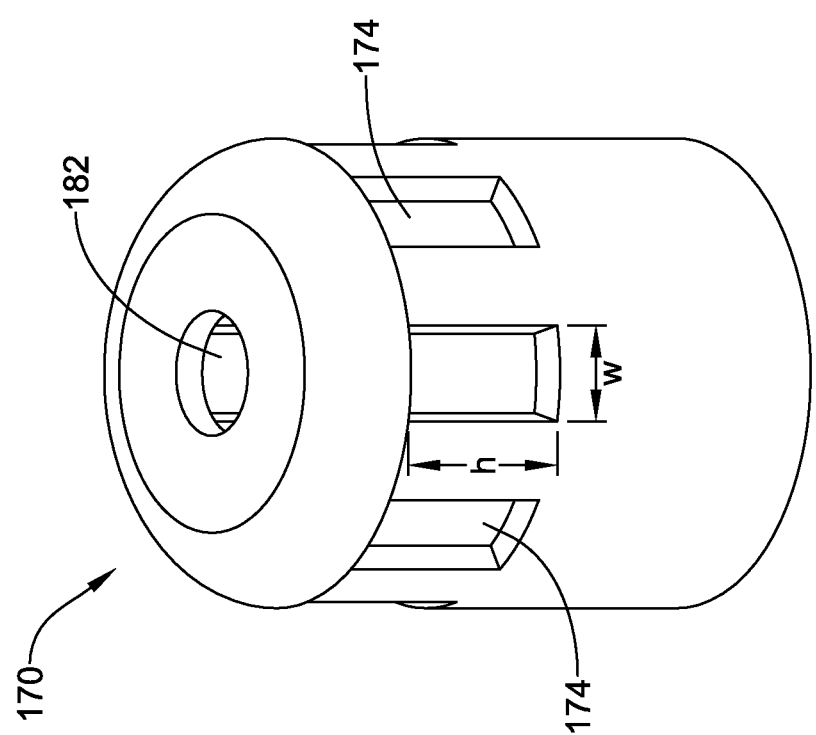
FIG. 4 is a schematic view of an exemplary distal cap.
Figure 5:
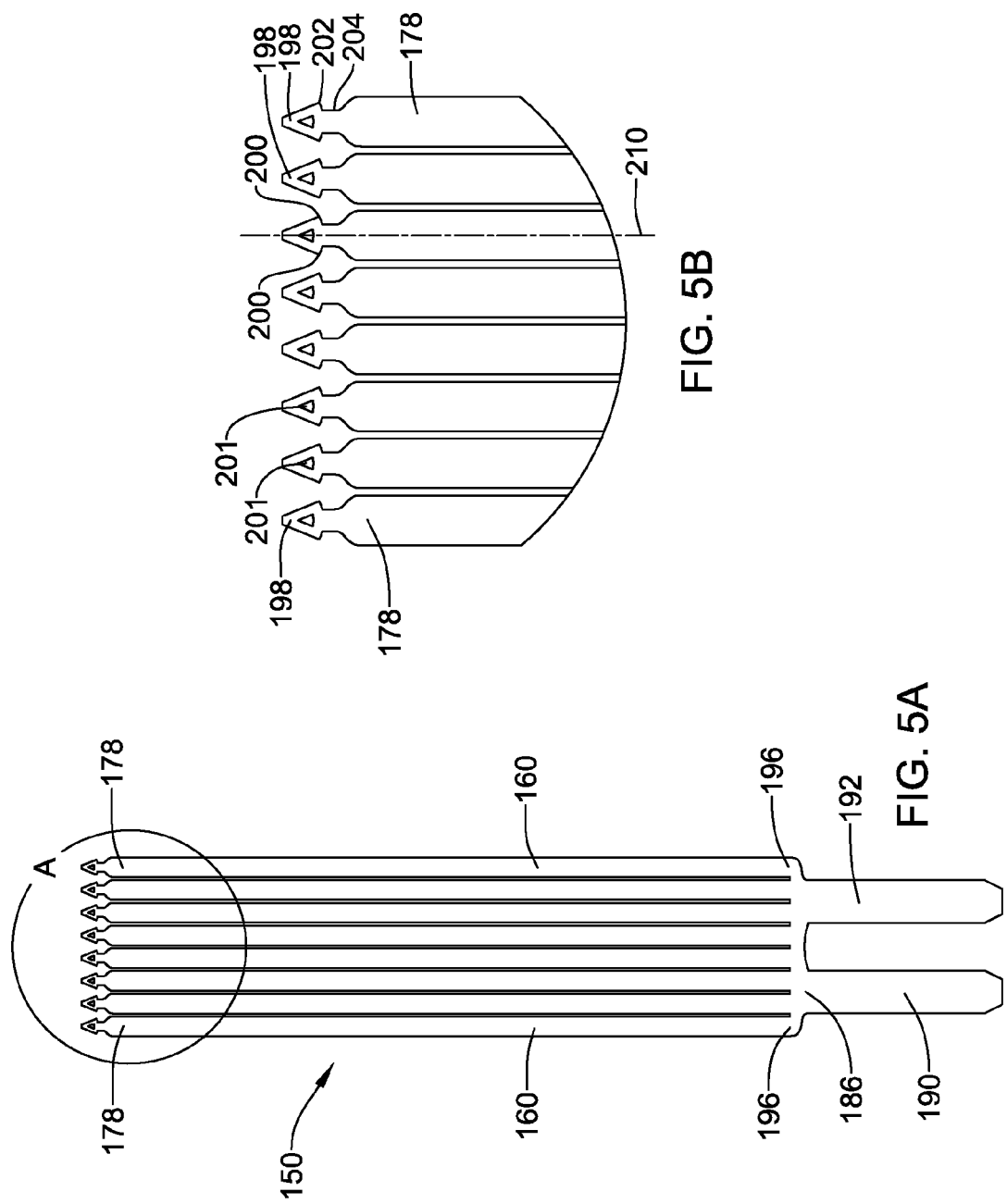
FIG. 5A is a schematic view of a flattened array of multiple flexible splines.
FIG. 5B is a close-up, schematic view of the distal ends of each of the splines of the flattened array shown in FIG. 5A.

FIG. 4 is a schematic view of an exemplary distal cap 170 that may be utilized in the construction of an exemplary expandable electrode assembly such as, for example, expandable electrode assembly 30, as described herein. FIG. 5A is a schematic view of a flattened array 150 of multiple flexible splines 160 that may be engaged with each of the slots 174 provided in the distal cap 170 to form an electrode assembly 30, and FIG. 5B is a close-up, schematic view of the distal ends 178 of each of the splines 160 of the flattened array 150.

In many cases, the distal cap 170 may be machined or laser cut from a metal or suitable plastic such that it has a desired size and shape. As shown in FIG. 4, the distal cap 170 may be fabricated such that it has a substantially hollow, cylindrical shape, and may include two or more slots 174 spaced an equal distance from one another about an outer circumference of the distal cap 170. In some cases, as shown in FIG. 4, each of the slots 174 may have a height h greater than a width w such that they are capable of receiving and retaining a distal end 178 of a respective flexible spline 160 when the distal end 178 of the flexible spline is inserted into the slot 174. The distal end of the distal cap 170 may be rounded such that it provides the catheter 10 with an atraumatic distal tip. In addition, the distal cap 170 may include a distal aperture 182, but this is not required. The aperture 182 may facilitate an introduction of an adhesive or other suitable potting material that may be provided as a secondary means of securing the distal ends 178 of each of the flexible splines 160 to the distal cap 170. In some cases, during construction of any one of the electrode assemblies, as described herein, a cylindrical tube, plug, or gasket may be inserted into the interior cavity of the distal cap to seal any remaining gaps between the splines and the slots subsequent to assembly. Alternatively, the distal end of the distal cap 170 may be solid.

Turning now to FIGS. 5A and 5B, the flattened array 150 of multiple flexible splines 160 may be initially fabricated as a flexible, multi-layered sheet including at least one flexible printed circuit bonded to a substrate. In some cases, the multi-layered sheet includes a first flexible printed circuit bonded to an upper surface of a substrate and a second flexible printed circuit bonded to a lower surface of the same substrate such that each of the flexible splines 160, when formed, have at least one electrode located on an outer surface and at least one electrode located on an inner surface of each of the splines 160. The substrate may include a shape memory material. This is just one example. The flexible multi-layered sheet including the flexible printed circuit is then laser cut or die cut in a direction along its longitudinal axis to form each of the individual, flexible splines 160. For example, the flexible multi-layered sheet including the flexible printed circuit is then laser cut or die cut to separate and form two or more flexible splines. In other cases, the flexible multi-layered sheet may be fabricated from a dual-sided flexible printed circuit having electrodes located both an upper surface and a lower surface.

The various materials used to fabricate the flexible multi-layered sheet from which the flexible splines 160 are formed may be selected such that each of the flexible splines 160 has a desired flexibility profile. The materials used to fabricate the flexible multi-layered sheet from which the flexible splines 160 are formed may be selected such that the flexible splines 160 are capable of some degree of deformation so that they can be twisted, rotated, and/or bent to facilitate insertion of their distal end into a distal cap (e.g. distal cap 170) during construction of an electrode assembly such as, for example, electrode assembly 30. In some cases, at least one of the layers or substrates of the multi-layered flexible sheet may include a shape memory material such as, for example, Nitinol or another super-elastic material. Incorporation of a Nitinol or super-elastic layer or substrate into the flexible multi-layered sheet from which the flexible splines 160 may be formed may provide the splines 160 with a degree of flexibility and deformation needed such that they can be twisted or rotated about a major axis to facilitate insertion of their distal end into a distal cap (e.g. distal cap 170) during construction of an electrode assembly such as, for example, electrode assembly 30.

In some cases, as shown in FIG. 5A, each of the flexible splines 160 extend from a proximal band 186 to which they are attached or integrally formed with at their proximal ends 196 to a free distal end 178. Two or more tabs 190, 192 may extend from the proximal band 186. Traces on the flexible printed circuit including those connected to the electrodes may terminate to pads bonded on an inner and/or outer surface of the two or more tabs 190, 192. In addition, the two or more tabs 190, 192 and may be utilized to couple to the electrode assembly 30 to the distal end 32 of the catheter body 34. Alternatively, both the proximal ends 196 and the distal ends 178 may be detached from one another. The splines 160 may be independent of one another, and may be inserted into the distal cap 170 and distal end 32 of the catheter body 34 either simultaneously or sequentially.

Each of the distal ends 178 of the flexible splines 160 may be formed by laser cutting, die cutting or other suitable method such that they define a locking feature 198 that is configured to be inserted into and secured within each of the slots 174 of the distal cap 170. Is some cases, the locking feature 198 may be defined by a geometrical shape having a first portion 202 having a first width and a second portion 204 having a second width. The first width can be greater than the second width. For example, as shown in FIGS. 5A and 5B, the locking feature 198 may have an arrowhead shape. In addition, each of the locking features 198 may include an aperture 201. An adhesive, when utilized, may permeate the apertures 201 and may provide a further means of securing the distal ends 178 to the distal cap 170.

In some cases, the material(s) from which the flattened array 150 may be sufficiently deformable such that the locking feature 198 is capable of being deformed for insertion into the corresponding slot 174 of the distal cap 170. For example, the points 200 of the arrowhead shaped locking feature 198, best viewed in FIG. 5B, may be capable of bending or folding inward towards a centerline 210 when inserted into a slot 174 of a distal cap 170. Once inserted into the slot 174, the material from which the flexible splines 160 is fabricated may be sufficiently resilient such that the arrowhead-shaped locking feature 198 returns to its unfolded or uncompressed state, mechanically securing the distal end 178 of the flexible spline 160 in the slot 174 such that the distal end 178 of the spline is unable to be disengaged or removed from the slot 174.

Figure 6:
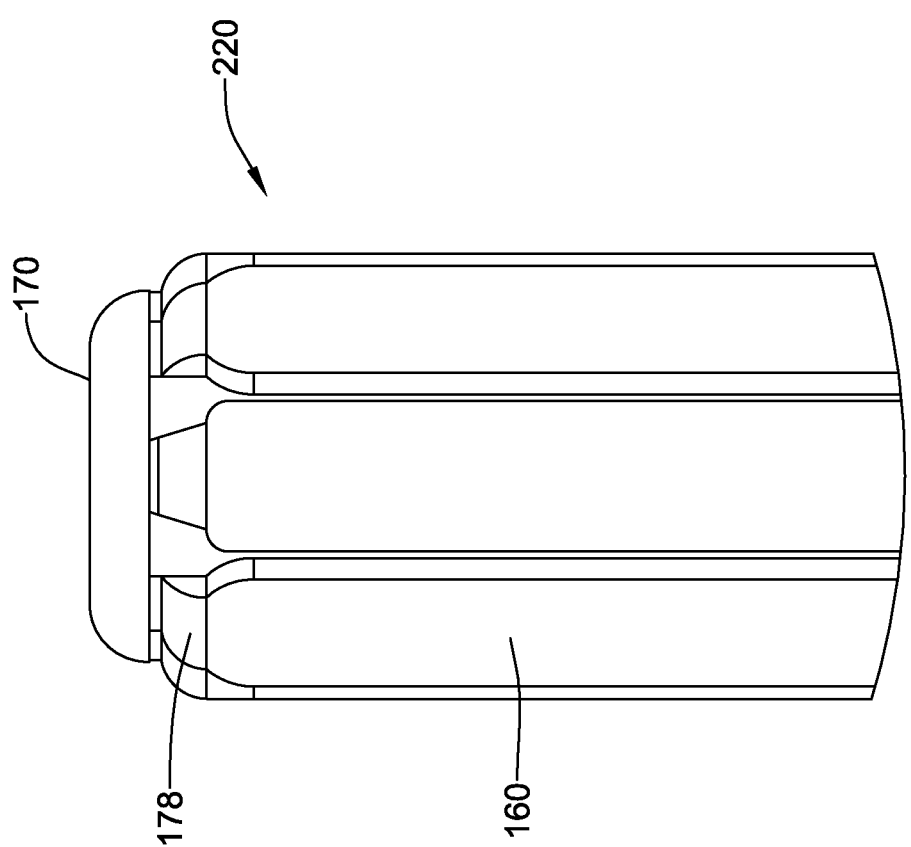
FIG. 6 is a close-up, schematic view of a distal portion of an electrode assembly showing the distal ends of multiple flexible splines engaged with a distal cap.

FIG. 6 is a detailed view of a distal portion 220 of an exemplary electrode assembly showing the distal ends 178 of a plurality of flexible splines 160 engaged with the distal cap 170.

Figure 7:
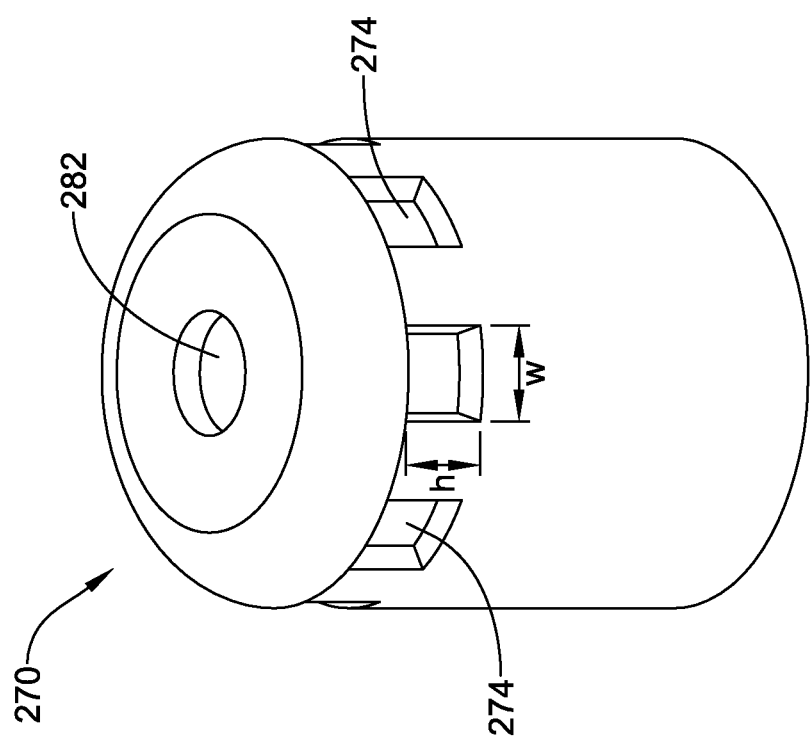
FIG. 7 is a schematic view of another exemplary distal cap.

FIG. 7 is a schematic view of another exemplary distal cap 270 that may be utilized in the construction of an exemplary expandable electrode assembly such as, for example, expandable electrode assembly 30, as described herein. FIG. 8A is a schematic view of another exemplary flattened array 250 of multiple flexible splines 260 that may be engaged with each of the slots 274 provided in the distal cap 270 to form an electrode assembly, and FIG. 8B is a close-up, schematic view of the distal ends 278 of each of the splines 260 of the flattened array 250.

In many cases, as described previously herein, the distal cap 270 may be machined or laser cut from a metal or suitable plastic such that it has a desired size and shape. As shown in FIG. 7, the distal cap 270 may be fabricated such that it has a substantially cylindrical shape defining an interior cavity, and may include two or more slots 274. In some cases, the two or more slots 274 may be spaced an equal distance from one another about an outer circumference of the distal cap 270 about the same longitudinal line. In other cases, the distance between the two or more slots 274 may vary. As shown in FIG. 7, each of the slots 274 may have a width w greater than a height h such that they are capable of receiving and retaining a distal end 278 of a respective flexible spline 260 when the distal end 278 of the flexible spline 260 is inserted into the slot 274. The distal end of the distal cap 270 may be rounded such that it provides the catheter 10 with an atraumatic distal tip. In addition, the distal cap 270 may include a distal aperture 282, but this is not required in all embodiments. The aperture 282, if provided, may facilitate an introduction of an adhesive or other suitable potting material that may be provided as a secondary means of securing the distal ends 278 of each of the flexible splines 260 to the distal cap 270. Alternatively, the distal end of the distal cap 270 may be solid. In some cases, during construction of the electrode assembly, a cylindrical tube, plug, or gasket may be inserted into the interior cavity of the distal cap 270 to seal any remaining gaps between the splines 260 and the slots 274.

As previously described herein, the flattened array 250 of multiple flexible splines 260 may be initially fabricated as a flexible, multi-layered sheet including at least one flexible printed circuit bonded to a substrate. In some cases, the multi-layered sheet includes a first flexible printed circuit bonded to an upper surface of a substrate and a second flexible printed circuit bonded to a lower surface of the same substrate such that each of the flexible splines 260, when formed, have at least electrode located on an outer surface and at least one electrode located on an inner surface of each of the splines 260. This is just one example. In other cases, the flexible multi-layered sheet may be fabricated from a dual-sided flexible printed circuit having electrodes located both an upper surface and a lower surface. The flexible multi-layered sheet including the flexible printed circuit(s) is then laser cut or die cut in a direction along its longitudinal axis to form each of the individual, flexible splines 260.

The various materials used to fabricate the flexible multi-layered sheet from which the flexible splines 260 are formed may be selected such that each of the flexible splines 260 has a desired flexibility profile. The materials used to fabricate the flexible multi-layered sheet from which the flexible splines 260 are formed may be selected such that the flexible splines 260 are capable of some degree of deformation so that their distal end can be elastically inserted into a distal cap (e.g. distal cap 70) during construction of an electrode assembly such as, for example, electrode assembly 30. In some cases, at least one of the layers of the multi-layered flexible sheet may include Nitinol or another super-elastic material. Incorporation of a Nitinol or super-elastic layer or substrate into the flexible multi-layered sheet from which the flexible splines 260 may be formed may provide the splines 260 with a degree of mechanical strength, flexibility and deformation needed such that their distal end can be inserted into a distal cap (e.g. distal cap 270), causing the distal barb 302 to bend inward and then recover to lock the spline in position during construction of an electrode assembly such as, for example, electrode assembly 30.

In some cases, as shown in FIG. 8A, each of the flexible splines 260 extend from a proximal band 286 to which they are attached or integrally formed with at their proximal ends 296 to a free distal end 278. Two or more tabs 290, 292 may extend from the proximal band 286. Traces on the flexible printed circuit including those connected to the electrodes may terminate to pads bonded on an inner and/or outer surface of the two or more tabs 290, 292. In addition, the two or more tabs 290, 292 and may be utilized to couple to the electrode assembly 30 to the distal end 42 of the catheter body 34. Alternatively, both the proximal ends 296 and the distal ends 278 may be freely detached from one another.

Each of the distal ends 278 of the flexible splines 260 may be formed by laser cutting, die cutting or other suitable method such that they define a locking feature 298 that is configured to be inserted into and secured within each of the slots 274 of the distal cap 270. Is some cases, the locking feature 298 may be defined by a geometrical shape having a first portion 302 having a first width and a second portion 304 having a second width. The first width can be greater than the second width. For example, as shown in FIGS. 8A and 8B, the locking feature 298 may have a barb or hook shape.

In some cases, the material(s) from which the flattened array 250 may be sufficiently deformable such that the locking feature 298 is capable of being deformed for insertion into the corresponding slot 274 of the distal cap 270. For example, the first portion 302 of the barb or hook shaped locking feature 298 may be capable of bending or flexing inward towards a centerline 310 when inserted into a slot 274 of a distal cap 270. Once inserted into the slot 274, the material from which the flexible splines 260 is fabricated may be sufficiently resilient such that the hook or barbed-shaped locking feature 298 returns to its uncompressed state, mechanically securing the distal end 278 of the flexible spline 260 in the slot 274 such that the distal end 278 of the spline is unable to be disengaged or removed from the slot 274.

Figure 9A:
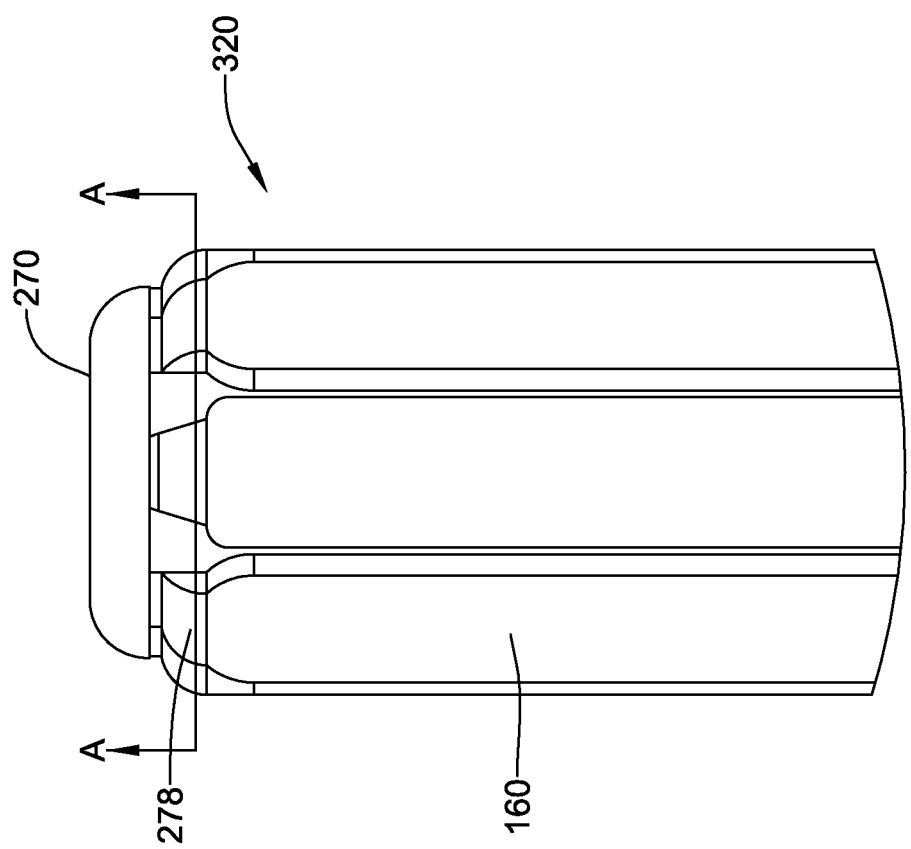
FIG. 9A is a detailed view of a distal portion of an exemplary electrode assembly showing the distal ends of a plurality of flexible splines engaged with a distal cap 170.

FIG. 9A is a detailed view of a distal portion 320 of an exemplary electrode assembly showing the distal ends 278 of a plurality of flexible splines 160 engaged with the distal cap 170. FIG. 9B is a cross-sectional view of the distal portion 320 taken along lines A-A of FIG. 9A and shows the first portions 302 of the barb-shaped locking features 298 engaged in the slots 274 of distal cap 270.

In some cases, during construction of any one of the electrode assemblies, as described herein, a cylindrical tube, plug, or gasket 356 may be inserted into the interior cavity 358 of the distal cap 370 to seal any remaining gaps between the splines 360 and the slots 374 subsequent to assembly.

FIG. 10 is a cross sectional view of a distal portion 370 of an exemplary electrode assembly including a cylindrical tube, plug, or gasket 356.

Figure 11:
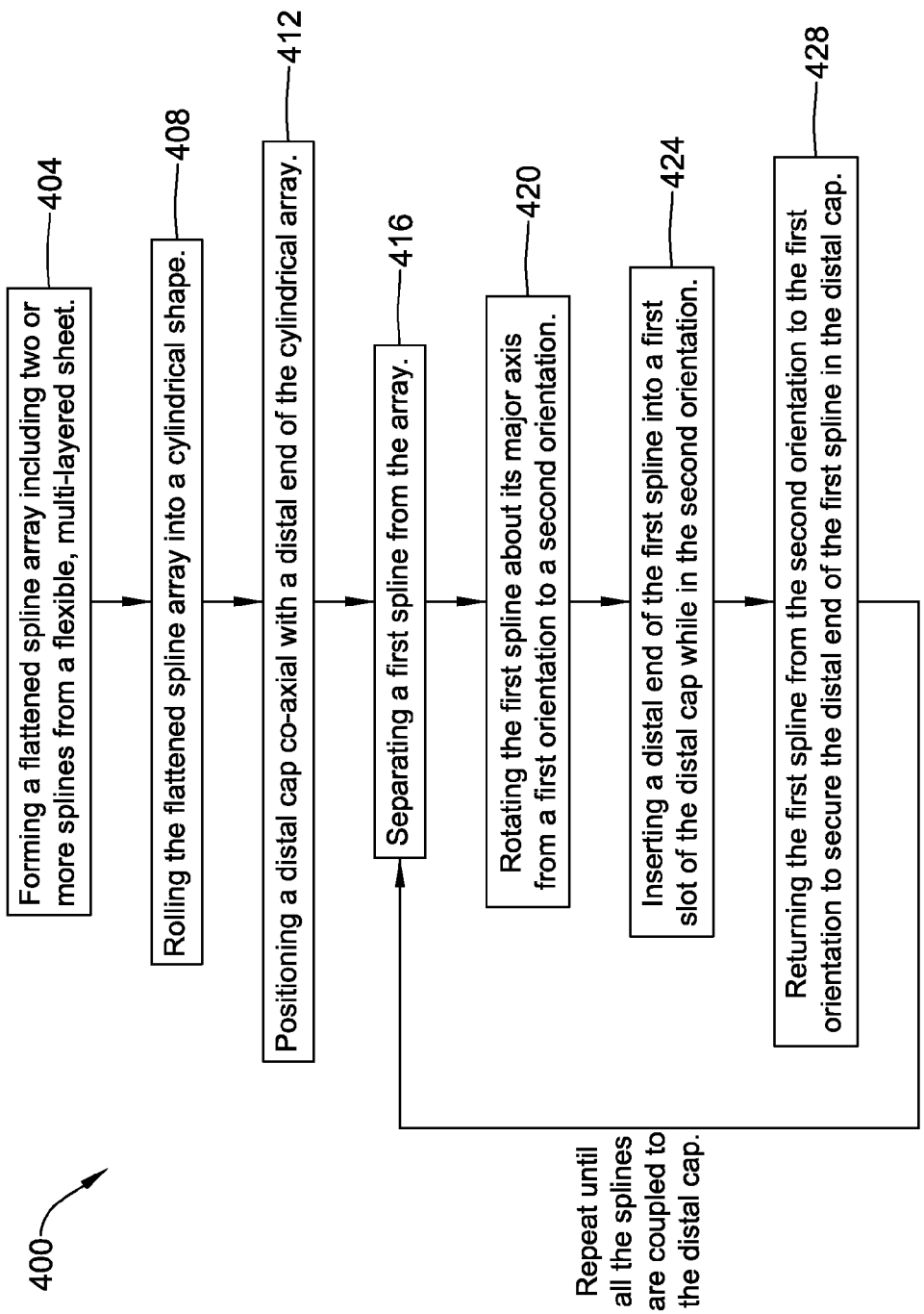
FIG. 11 is a flow chart of a method of constructing an exemplary electrode assembly.

FIG. 11 is a flow chart of a method 400 of constructing an expandable electrode assembly using a distal cap and a flexible spline array, as described herein. The method 400 may be automated using appropriate machinery or manually performed by an individual. During assembly, a flattened spline array may be formed from flexible, multilayered sheet (Block 404). As described herein, the flexible, multi-layered sheet from which a flattened spline array may be formed may includes at least one flexible printed circuit bonded to a substrate. In some cases, the multi-layered sheet includes a first flexible printed circuit bonded to an upper surface of a substrate and a second flexible printed circuit bonded to a lower surface of the same substrate such that each of the flexible splines, when formed, have at least electrode located on an outer surface and at least one electrode located on an inner surface of each of the splines. The individual splines may be formed by laser cutting or die cutting the flexible multi-layered sheet in a direction along its longitudinal axis to form the flattened spline array. In many cases, the flattened spline array includes at least two splines. Next, the flattened spline array including the two or more splines may be rolled into cylindrical shape (Block 408). In some cases, the flattened spline array may be rolled around a mandrel or other cylindrical member to facilitate formation of the cylindrical shape. A band may also be placed around the array to maintain its cylindrical shape during assembly.

Figure 12:
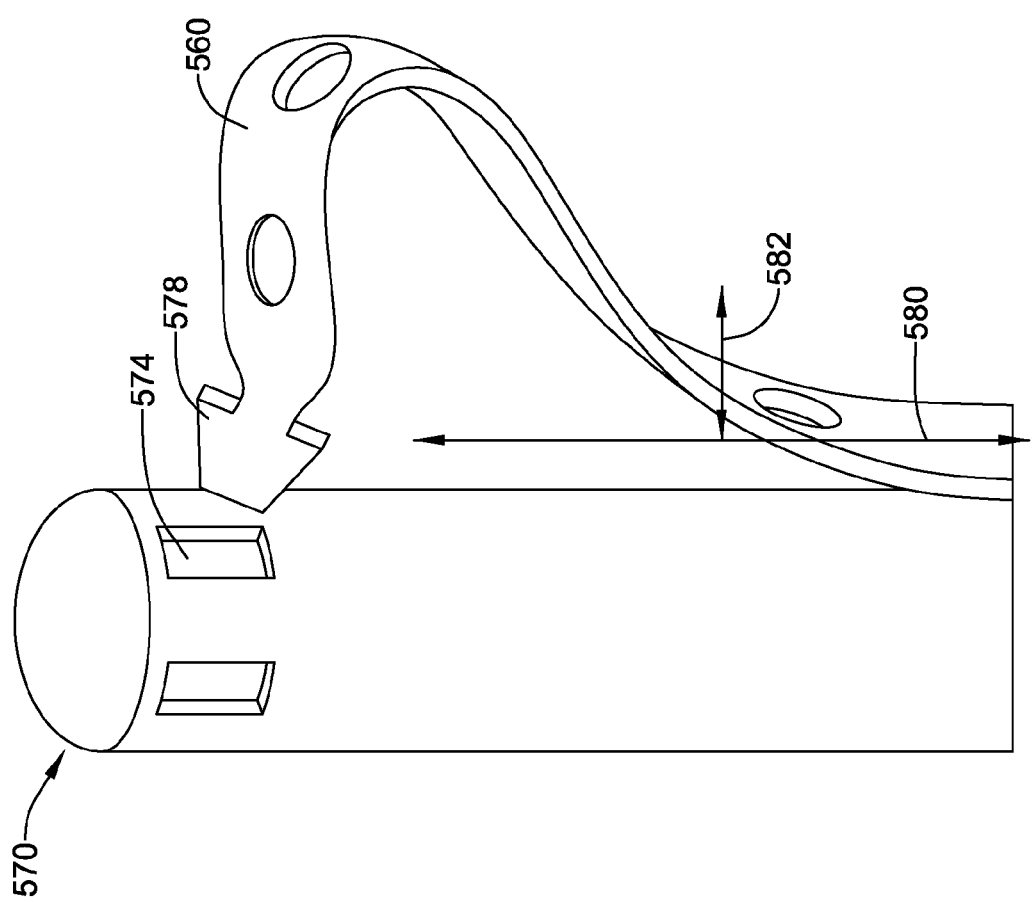
FIG. 12 is a schematic view of an exemplary, individual spline being rotated about its major axis and bent about its minor axis such that the distal end of the spline can be engaged within a slot provided in an exemplary distal cap.

A distal cap such as those described herein may be positioned adjacent a distal end of the now cylindrical array such that the distal cap is co-axial with the cylindrical array (Block 412). A first spline may be separated from the other splines of the array (Block 416) and rotated or twisted about its major axis and bent about its minor axis from a first orientation to a second orientation (Block 420). In some cases, the first spline may be rotated at about 60 to about 120 degrees about its major axis and more particularly, about 90 degrees about its major axis from a first orientation to a second orientation. The spline may also be bent about its minor axis to align with one of the slots in the distal tip 570. The spline should be rotated a sufficient degree of rotation about its major and minor axes such that the distal end of the locking feature is capable of being inserted into a corresponding slot provided in the distal cap. In some cases, as described herein, the distal end of the spline including the locking feature may be deformed so as to facilitate insertion of the distal end of the spline into the slot. These steps are schematically illustrated in FIG. 12. FIG. 12 shows a spline 560 being twisted or orientated about its major axis 580 and bent about its minor axis 582 such that the distal end 578 may be inserted into slot 574 provided in distal cap 570.

The distal end of the spline may then be inserted into a slot provided in the distal cap while still in the second orientation (Block 420). Once inserted through the slot, the locking feature may re-assume its un-deformed shape, if applicable. In addition, the spline may be returned from its second orientation to its first orientation and lie flat in the slot (Block 428). In some cases, the spline may be manually twisted or rotated in the slot from its second orientation to its first orientation. In other cases, because of the elasticity of some of the materials used to construct the flexible, multi-layer sheet from which the spline array is formed, the spline may be configured to automatically return from its second orientation to its first orientation and lie flat in the slot. The spline may be mechanically interlocked with the cap by the locking feature formed at the distal end of the spline. The remaining splines may be engaged with the cap following the same steps outlined by Blocks 416, 420, 424, and 428. The proximal ends of the splines may be banded together, and may be anchored or bonded to a distal portion of the catheter body.

In another case, the splines may be fully separated from one another such that they are not connected. Each of the distal ends of the separated splines may be inserted into a corresponding slot provided in the distal cap. The distal ends of the separated splines may be mechanically interlocked with the cap by the locking feature formed at the distal end of the spline. Some rotation of the individual splines may be necessary to urge the locking feature into slot after which the spline may lie flat in the slot. The remaining individual splines may be engaged with the cap utilizing the same method.

In some cases, an adhesive may be used to further secure the distal ends of the spline with the cap. For example, the distal cap may include an aperture through which an adhesive or other suitable potting material may be introduced. A cylindrical tube, plug, or gasket may also be inserted into the proximal end of the cap, occluding the gaps proximal to the distal ends of the splines. In addition or in alternative to, a sealing material may be provided to seal any gaps between the distal ends of the splines and the slots such that the outer surface of the distal cap is substantially smooth and does not provide a surface onto which blood may collect and thrombi form.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A catheter comprising:
   an elongate catheter body extending from a proximal end to a distal end;
   an expandable electrode assembly disposed at the distal end of the catheter body, the electrode assembly comprising a plurality of flexible splines extending from the distal end of the catheter body to a distal cap;
   wherein the distal cap comprises a plurality of slots disposed about an outer circumference of the distal cap, and a cylindrical shape defining an interior cavity;
   wherein the plurality of flexible splines include a first spline comprising a distal end defining a locking feature secured within one of the plurality of slots provided in the distal cap, the locking feature comprising an aperture formed therein, the expandable electrode assembly configured to be transitioned between a collapsed configuration suitable for delivery and an expanded configuration; and
   two or more electrodes located on the first spline; and
   an adhesive disposed within the distal cap to further secure the locking feature.

2. The catheter according to claim 1, wherein the distal cap comprises a rounded tip having an aperture defined therein.

3. The catheter according to claim 1, wherein a height is greater than a width for each of the slots.

4. The catheter according to claim 1, wherein the locking feature defined by the distal end of the first spline comprises a first portion having a first width and a second portion having a second width, the first width greater than the second width.

5. The catheter according to claim 1, wherein the distal cap comprises a rounded distal end and defines an atraumatic distal tip of the catheter.

6. The catheter according to claim 1, wherein each of the slots are spaced an equal distance from one another about the outer circumference of the distal cap.

7. The catheter according to claim 1, further comprising an actuation member coupled to the expandable electrode assembly.

8. The catheter according to claim 1, wherein the locking feature defined by the distal end of the first spline comprises an arrowhead shape.

9. The catheter according to claim 1, wherein the distal cap serves as a distal tip electrode.

10. A catheter comprising:
    an elongate catheter body extending from a proximal end to a distal end;
    an expandable electrode assembly disposed at the distal end of the catheter body, the electrode assembly comprising a plurality of flexible splines including a first spline extending from the distal end of the catheter body to a distal cap, the distal cap comprising a cylindrical shape defining an interior cavity and a plurality of slots including a first slot disposed about an outer circumference of the distal cap, the first spline comprising a distal end defining a locking feature secured within the first slot, the locking feature comprising an aperture formed therein, the interior cavity of the distal cap containing an adhesive to further secure the locking feature, the expandable electrode assembly configured to be transitioned between a collapsed configuration suitable for delivery and an expanded configuration
    two or more electrodes located on the first spline; and
    an actuation member coupled to the expandable electrode assembly.

\* \* \* \* \*